(12) United States Patent
Tuszynski et al.

(10) Patent No.: US 7,265,248 B1
(45) Date of Patent: Sep. 4, 2007

(54) COMPOSITIONS AND METHODS FOR THE TREATMENT OF MALARIA

(75) Inventors: Jack A. Tuszynski, Edmonton (CA); Stephen H. Curry, Rochester, NY (US)

(73) Assignee: Technology Innovations, LLC, Pittsford, NY (US)

( * ) Notice: Subject to any disclaimer, the term of this patent is extended or adjusted under 35 U.S.C. 154(b) by 0 days.

(21) Appl. No.: 11/412,823

(22) Filed: Apr. 28, 2006

Related U.S. Application Data

(60) Provisional application No. 60/676,113, filed on Apr. 29, 2005.

(51) Int. Cl.
 C07C 49/547 (2006.01)
 C07C 49/553 (2006.01)
 C07C 49/563 (2006.01)
 A61K 31/12 (2006.01)

(52) U.S. Cl. .................. 568/326; 568/329; 568/330; 514/680

(58) Field of Classification Search .................. None
 See application file for complete search history.

(56) References Cited

U.S. PATENT DOCUMENTS

| | | | |
|---|---|---|---|
| 3,876,632 A | 4/1975 | Sturm et al. |
| 4,451,674 A | 5/1984 | Kobayashi et al. |
| 4,467,126 A | 8/1984 | Zinnen |
| 4,552,894 A | 11/1985 | Inoue et al. |
| 4,568,488 A | 2/1986 | Lee-Huang |
| 4,571,441 A | 2/1986 | Miwa et al. |
| 4,962,252 A | 10/1990 | Wade |
| 5,316,932 A | 5/1994 | Bigner et al. |
| 5,328,603 A | 7/1994 | Velander et al. |
| 5,362,857 A | 11/1994 | Hock |
| 5,466,620 A | 11/1995 | Bang |
| 5,470,822 A | 11/1995 | Younes |
| 5,549,840 A | 8/1996 | Mondin et al. |
| 5,580,898 A | 12/1996 | Trojanowski et al. |
| 5,593,958 A | 1/1997 | Mondin et al. |
| 5,599,785 A | 2/1997 | Mondin et al. |
| 5,614,500 A | 3/1997 | Zimmermann |
| 5,661,032 A | 8/1997 | Miller et al. |
| 5,670,691 A | 9/1997 | Spangler et al. |
| 5,679,530 A | 10/1997 | Brentani et al. |
| 5,731,281 A | 3/1998 | Mondin et al. |
| 5,827,679 A | 10/1998 | Moore et al. |
| 5,830,452 A | 11/1998 | Bauer et al. |
| 5,851,789 A | 12/1998 | Simon et al. |
| 5,886,025 A | 3/1999 | Pinney |
| 6,000,772 A | 12/1999 | Miller et al. |
| 6,025,331 A | 2/2000 | Moses et al. |
| 6,162,930 A | 12/2000 | Pinney et al. |
| 6,177,472 B1 | 1/2001 | Wilson et al. |
| 6,222,093 B1 | 4/2001 | Marton et al. |
| 6,232,089 B1 | 5/2001 | Buckle et al. |
| 6,258,841 B1 | 7/2001 | Uckun et al. |
| 6,306,615 B1 | 10/2001 | Beckmann et al. |
| 6,329,420 B1 | 12/2001 | Uckun et al. |
| 6,346,389 B1 | 2/2002 | Altieri |
| 6,346,408 B1 | 2/2002 | Chueh |
| 6,350,777 B2 | 2/2002 | Pinney et al. |
| 6,358,957 B1 | 3/2002 | Fukumoto et al. |
| 6,372,772 B1 | 4/2002 | Kirkpatrick et al. |
| 6,423,735 B1 | 7/2002 | Camden et al. |
| 6,423,736 B1 | 7/2002 | Camden et al. |
| 6,433,187 B1 | 8/2002 | Clark et al. |
| 6,441,053 B1 | 8/2002 | Klein et al. |
| 6,451,807 B1 | 9/2002 | Emmick et al. |
| 6,458,847 B1 | 10/2002 | Wilson et al. |
| 6,462,062 B1 | 10/2002 | Camden et al. |
| 6,472,541 B2 | 10/2002 | Tsien et al. |
| 6,482,043 B1 | 11/2002 | Stout |
| 6,576,219 B2 | 6/2003 | Brandt et al. |
| 6,579,577 B2 | 6/2003 | Kondo et al. |
| 6,586,188 B1 | 7/2003 | Berggren et al. |
| 6,593,374 B2 | 7/2003 | Pinney et al. |
| 6,608,096 B1 | 8/2003 | Camden et al. |
| 6,620,818 B1 | 9/2003 | Davis |
| 6,630,492 B1 | 10/2003 | Bauer et al. |
| 6,635,434 B1 | 10/2003 | Jakobsen et al. |
| 6,660,767 B2 | 12/2003 | Jacobs et al. |
| 6,676,944 B2 | 1/2004 | Dalton et al. |
| 6,710,065 B1 | 3/2004 | Camden et al. |
| 6,713,480 B2 | 3/2004 | Fukumoto et al. |
| 6,720,349 B2 | 4/2004 | Quada, Jr. et al. |
| 6,750,330 B1 | 6/2004 | Davis et al. |
| 6,846,481 B1 | 1/2005 | Gaertig et al. |

(Continued)

OTHER PUBLICATIONS

Banerjee, A. et al., "Preparation of a Monoclonal Antibody Specific for the Class IV Isotype of Beta-Tubulin. Purification and Assembly of Alpha-beta II, Alpha/beta III, and Alpha/beta IV Tubulin Dimers from Bovine Brain" *J. Biol. Chem.* (1992) 267(8):5625-5630, The American Society for Biochemistry and Molecular Biology, Inc. USA.

Banerjee, A. et al. "Differential Effects of Colchicine and its B-ring Modified Analog MTPT on the Assembly-independent BTPase Activity of Purified b-tubulin Isoforms from Bovine Brain," *Biochem. Biophys. Res. Commun.* (1997) 231:698-700, Academic Press.

Chaudhuri, A.R. et al., "IKP104-Induced Decay of Tubulin: Role of the A-Ring Binding Site of Colchicine," *Biochemistry* (1998) 37:17157-17162, American Chemical Society.

(Continued)

*Primary Examiner*—Sikarl A. Witherspoon
(74) *Attorney, Agent, or Firm*—Buchanan Ingersoll & Rooney PC

(57) ABSTRACT

A colchicine derivative and a method of using a colchicine derivative as a pharmacological agent in the treatment of malaria are provided.

11 Claims, 1 Drawing Sheet

U.S. PATENT DOCUMENTS 6,964,436 B2  11/2005  Le Quere

OTHER PUBLICATIONS

Khan, Israr A. et al., "Differential Interaction of Tubulin Isotypes with the Antimitotic Compound IKP-104," (2000) *Biochemistry* 39:9001-9009, American Chemical Society.

Lowry, O.H. et al., "Protein Measurement with the Folin Phenol Reagent" *Biol. Chem.* (1951) 193:265-275.

Lu, Q. et al., "Structural and Functional Properties of Tubulin Isotypes," (1998) *Adv. Struct. Biol.* 5:203-227, JAI Press Inc.

Lu, Q. et al., "In Vitro Analysis of Microtubule Assembly of Isotypically Pure Tubulin Dimers. Intrinsic Differences in the Assembly Process of Alpha/beta II, Alpha/beta III, and Alpha/beta IV Tubulin Dimers in the Absence of Microtubule-associated Proteins" *J. Biol Chem.* (1994) 269(3):2041-2047, The American Society for Biochemistry and Molecular Biology, Inc.

Panda et al., "Excimer Fluorescence of Pyrene-Maleimide-Labeled Tubulin" *Eur. J. Biochm* (1992) 204:783-787, FEBS 1992.

Panda et al. "Microtubule Dynamics in Vitro are Regulated by the Tubulin Isotype Composition," *Proc. Nat. Acad. Sci. USA* (1994) 91:11358-11362.

Panda et al. "Stabilization of Microtubule Dynamics by Estramustine by Binding to a Novel Site in tubulin: A Possible Mechanistic Basis for its Antitumor Action" *PNAS USA* (1997) 94:10560-10564, The National Academy of Sciences.

Panda et al., "Suppression of Microtubule Dynamics by LY290181" *J. Biol. Chem* (1997) 272(12):7681-7687, The American Society for Biochemistry and Molecular Biology, Inc.

The Merck Index, p. 2438, Tenth Edition, Merck & Co., Inc., Rahway, New Jersey (1983).

FIG. 1

```
CLUSTAL W (1.83) multiple sequence alignment tr|Q04200              MREIVHVQAGQCGNQIGAKFWEVIS EGIDPSGTYRGDSDLQLERVDVFYNEATGGRYV
tr|Q7RCR6              MREIVHVQAGQCGNQIGAKFWEVIS EGIDPSGTYRGDSDLQLERVDVFYNEATGGRYV
sp|P14643|TBB_PLAFK    MREIVHIQAGQCGNQIGAKFWEVIS EGIDPSGTYCGDSDLQLERVDVFYNEATGGRYV
tr|Q25792              MREIVHIQAGQCGNQIGAKFSQVIS QGIDPSGTYCGDSDLQLERVDVFYNEATGGRYV
sp|P14140|TBB_PLAFA    MREIVHIQAGQCGNQIGAKFWEVIS EGIDPSGTYSGDSDLQLERVDVFYNEATGGRYV
sp|P07437|TBB1_HUMAN   MREIVHIQAGQCGNQIGAKFWEVIS EGIDPTGTYHGDSDLQLDRISVYYNEATGGKYV
                       ******:************* :**** :****:*** *******:*::*:*******:**

tr|Q04200              PRAILMDLEPGTMDSVRAGPFGQLFRPDNFVFGQTGAGNNWAKGHYTEGAELIDAVLDVV
tr|Q7RCR6              PRAILMDLEPGTMDSVRAGPFGQLFRPDNFVFGQTGAGNNWAKGHYTEGAELIDAVLDVV
sp|P14643|TBB_PLAFK    PRAILMDLEPGTMDSVRAGPFGQLFRPDNFVFGQTGAGNNWAKGHYTEGAELIDAVLDVV
tr|Q25792              PRAILMDLEPGTMDSVRAGPFGQLFRPDNFVFGQTGAGNNWAKGHYTEGAELIDAVLDVV
sp|P14140|TBB_PLAFA    PRAILMDLEPGTMDSVRAGPFGQLFRPDNFVFGQTGAGNNWAKGHYTEGAELIDAVLDVL
sp|P07437|TBB1_HUMAN   PRAILVDLEPGTMDSVRSGPFGQIFRPDNFVFGQSGAGNNWAKGHYTEGAELVDSVLDVV
                       *****:***********:*****:**********:*****************:*:****:

tr|Q04200              RKEAEGCDCLQGFQITHSLGGGTGSGMGTLLISKIREEY-DRIMGGVFPSPKVSDTVV
tr|Q7RCR6              RKEAEGCDCLQGFQITHSLGGGTGSGMGTLLISKIREEYPDRIMGGVFPSPKVSDTVV
sp|P14643|TBB_PLAFK    RKEAEGCDCLQGFQITHSLGGGTGSGMGTLLISKIREEYPDRIMGGVFPSPKVSDTVV
tr|Q25792              RKEAEGCDCLQGFQITHSLGGGTGSGMGTLLISKIREEYPDRIMGGVFPSPKVSDTVV
sp|P14140|TBB_PLAFA    RKEAEGCDCLQGFQITHSLGGGTGSGMGTLLISKIREEYPDRIMGGVFPSPKVSDTVV
sp|P07437|TBB1_HUMAN   RKEAESCDCLQGFQLTHSLGGGTGSGMGTLLISKIREEYPDRIMGGVVPSPKVSDTVV
                       ***.****:**************************. ******* tr|Q04200              EPYNATLSVHQLVENADEVQIDNEALYDICFRTLKLTTPTYGDLNHLVSAAMSGVTC
tr|Q7RCR6              EPYNATLSVHQLVENADEVQIDNEALYDICFRTLKLTTPTYGDLNHLVSAAMSGVTC
sp|P14643|TBB_PLAFK    EPYNATLSVHQLVENADEVQIDNEALYDICFRTLKLTTPTYGDLNHLVSAAMSGVTC
tr|Q25792              EPYNATLSVHQLVENADEVQIDNEALYDICFRTLKLTTPTYGDLNHLVSAAMSGVTC
sp|P14140|TBB_PLAFA    EPYNATLSVHQLVENADEVQIDNEALYDICFRTLKLTTPTYGDLNHLVSAAMSGVTC
sp|P07437|TBB1_HUMAN   EPYNATLSVHQLVENTDETQIDNEALYDICFRTLKLTTPTYGDLNHLVSGTMSGVTC
                       ***************:**:************:**:*************:*:****:

tr|Q04200              RFPGQLNADLRKLAVNLIPFPRLHFFMIG FAPLTSRGSQIAALTVPELTQQMFDAKNMM
tr|Q7RCR6              RFPGQLNADLRKLAVNLIPFPRLHFFMIG             ALTVPELTQQMFDAKNMM
sp|P14643|TBB_PLAFK    RFPGQLNADLRKLAVNLIPFPRLHFFMIG             ALTVPELTQQMFDAKNMM
tr|Q25792              RFPGQLNADLRKLAVNLIPFPRLHFFMIG             ALTVPELTQQMFDAKNMM
sp|P14140|TBB_PLAFA    RFPGQLNADLRKLAVNLIPFPRLHFFMYG             ALTVPELTQQMFDAKNMM
sp|P07437|TBB1_HUMAN   RFPGQLNADLRKLAVNVPPFPRLHFFMPG             ALTVPDLTQQVFDAKNMM
                       ****:*****:.******* *             ***::**** tr|Q04200              CASDPRHGRYLTVAAIFRGRMSTKEVDEQMLNVQNKNSSYFVEWIPNNVKTAVCDIPLKG
tr|Q7RCR6              CASDPRHGRYLTVAAIFRGRMSTKEVDEQMLNVQNKNSSYFVEWIPNNVKTAVCDI
sp|P14643|TBB_PLAFK    CASDPRHGRYLTVAAIFRGRMSTKEVDEQMLNVQNKNSSYFVEWIPNNVKTAVCDI
tr|Q25792              CASDPRNGRYLTVAAIFRGRMSTKEVDEQMLNVQNKNSSYFVEWIPNNVKTAVCDI
sp|P14140|TBB_PLAFA    CTSDPRHGRYLTVAAIFRGRMSTKEVDEQMLNVQNKNSSYFVEWIPNNVKTAVCDIFLG
sp|P07437|TBB1_HUMAN   AACDPRHGRYLTVAAVFRGRMSMKEVDEQMLNVQNKNSSYFVEWIPNNVKVAVCDIPPRG
                       .:.*:***:*** *********************: *:**:.* tr|Q04200              LKMAVTFIGNSTAIQEMFKRVSDQFTAMFRRKAFLHWYTGEGMDEMEFTEAESNM-DLVS
tr|Q7RCR6                     FIGNSTAIQEMFKRVSDQFTAMFRRKAFLHWYTGEGMDEMEFTEAESNMNDLVS
sp|P14643|TBB_PLAFK           FIGNSTAIQEMFKRVSDQFTAMFRRKAFLHWYTGEGMDEMEFTEAESNMNDLVS
tr|Q25792                     FIGNSTAIQEMFKRVSDQFTAMFRRKAFLHWYTGEGMDEMEFTEAESNMNDLVS
sp|P14140|TBB_PLAFA           FIGNSTAIQEMFKRVSDQFTAMFRRKAFLHWYTGEGMDEMEFTEAESNMNDLVS
sp|P07437|TBB1_HUMAN   LKMAVTFIGNSTAIQELFKRISEQFTAMFRRKAFLHWYTGEGMDEMEFTEAESNMNDLVS
```

COMPOSITIONS AND METHODS FOR THE TREATMENT OF MALARIA

CROSS-REFERENCE TO RELATED APPLICATION

This application claims the benefit of priority of U.S. Provisional Application No. 60/676,113 filed Apr. 29, 2005, the entire contents of which are incorporated by reference herein.

FIELD OF THE INVENTION

Provided are derivatives of colchicine for the treatment of malaria. Exemplary colchine derivatives can selectively bind to beta-tubulin isotypes that are preferentially expressed in *Plasmodium* species. Also provided are methods for using derivatives of colchicine for the treatment of malaria in mammals and humans.

BACKGROUND

As discussed in U.S. Pat. No. 6,846,481, malaria is caused by parasitic protozoa of the genus *Plasmodium*, and is responsible for approximately two-million deaths each year worldwide. Current control efforts are focused on the mosquito vector, and treatment of the disease with anti-malarial drugs. No vaccine is yet available. Over the past four decades, the parasite has become increasingly resistant to many anti-malarial drugs and an effective vaccine is seen as a promising means for controlling morbidity and mortality caused by this pathogen. Most of the candidate molecules from *Plasmodium* suggested for inclusion in a vaccine are proteins that bind to receptors of host target cells. Necessary for vaccine development is the identification and characterization of the role played by these proteins. Unfortunately, this effort has been hampered by difficulties in procuring enough parasite protein to allow thorough study. Several heterologous expression systems have been utilized but none has proven to be ideal, especially for the production of functional protein.

A variety of agents have been proposed for the treatment of malaria. Many of these agents have distinct disadvantages, including the ability of the malarial parasite to develop drug resistance to the agents.

Since the discovery of quinine, a variety of agents utilizing various biochemical mechanisms have been used to treat malaria. For example, dihydrofolate reductase inhibitors (e.g., diaminopyrimidines), oxygen-reduction mediators (e.g., primaquine), and antibacterial agents (e.g., sulphonamides) have been administered to treat the disease.

Existing agents have or have had their place in the therapeutic armamentarium with varying degrees of success, however, several types of deficiencies can be identified in the available drugs currently available for the treatment of malaria. In particular, since 1960 the transmission of malaria has risen in most regions where the infection is endemic, and chloroquine-resistant and multi-drug resistant strains of, e.g., *P. falciparum*, have spread. In addition, current antimalarial drugs are typically accompanied by side effects, including rash, vomiting, diarrhea, fever and headache (atovaquone and mefloquine); cardiovascular and CNS effects (chloroquine); and blood dyscrasias (pyrimethamine and primaquine). Pharmacokinetics are typically sub-optimal with long half life values (e.g., atovaquone, 1.5-3 days; chloroquine, days to weeks; pyrimethamine, 80-95 hours; mefloquine, 20 days), excessive protein binding (e.g., 99% with atovaquone; ~98% with mefloquine), double peaking (e.g., atovaquone), massive volumes of distribution (chloroquine over 100 l/kg; mefloquine, several times the volume of body water), and erratic and incomplete absorption of oral doses.

Provided is a novel mechanistic approach to antimalarial drugs by inactivation of the microtubules of *P. falciparum* and *P. vivax*, as a component of the search for treatments with, for example, lesser risk of resistance, better safety profiles, and optimized pharmacokinetic properties.

Of the current drugs on the market used to treat malaria, none specifically target the plasmodial microtubules involved in mitosis. Microtubules are cylindrical organelles that play critical roles in mitosis, transport and cell mobility. They contain the protein tubulin. Tubulin molecules line up into protofilaments, thirteen (13) of which are arranged side to side to form the microtubule. In mitosis, the chromosomes are attached to microtubules, which constitute the mitotic spindle. In cell transport, organelles being moved are carried along the microtubule by motor proteins such as dynein or kinesin. A key aspect of microtubule function is the fact that microtubules exhibit dynamic behavior, in other words, they constantly grow and shrink. Targeting tubulin has been a successful strategy in the search for drugs for cancer, e.g. paclitexel (taxol) and the Vinca alkaloids. They work by inhibiting dynamic behavior, causing cells to undergo apoptosis. Only 2-5 drug molecules per microtubule are typically needed.

SUMMARY

There are multiple reasons why targeting tubulin can be effective to yield an antimalarial. First, plasmodia have tubulin, which is critical for their survival. Secondly, plasmodial tubulin is quite different from human tubulin, so that the colchicine derivatives of the present invention are capable of distinguishing between them. By such selectivity, in an exemplary embodiment, side effects on human cells from use of the colchicine derivatives can be reduced or eliminated. The colchicine derivative can poison the plasmodial microtubules and in an exemplary embodiment, relatively small doses can be effective. Furthermore, tubulin mutations and drug resistance are believed to be relatively rare or non-existent because the tubulin molecule typically has numerous constraints on its potential for variability: it typically has to polymerize into a 13-sided cylinder; once polymerized the tubulin molecule typically has to interact with a large number of other proteins to carry out its various functions; and the tubulin molecule typically has to form a highly complex flagellum with doublet and singlet microtubules, constituting an axoneme with approximately 200 other proteins. Tubulin typically cannot tolerate much variation. In addition, humans have 7 alpha-tubulin and 8 beta-tubulin isotypes—most anti-tubulin drugs target beta-tubulin. Plasmodia only have a few beta-tubulins. Thus, if one or more of these beta-tubulins is knocked out by a drug, the parasite has few if none other isotype to take its place. We have constructed models of *Plasmodium* and of the human tubulins, as well as of several other Apicomplexan tubulins (*Toxoplasma, Leishmania, Trypanosorna*). These models were derived from that of Löwe.

According to one aspect, a colchicine derivative represented by one of the following Formulas 1 to 7 is provided:

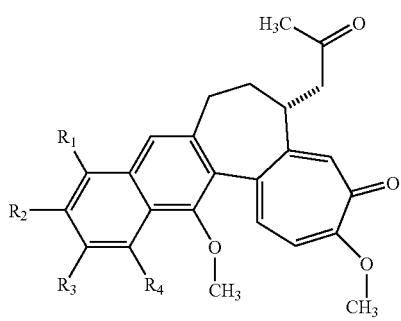

Formula 1 wherein $R_1$ to $R_4$ individually represent a hydrogen or a substituent;

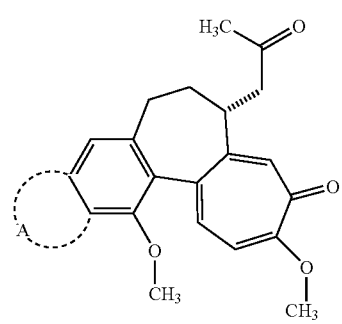

Formula 2 wherein A represents atoms for forming a cycloalkane ring, wherein A is substituted or unsubstituted;

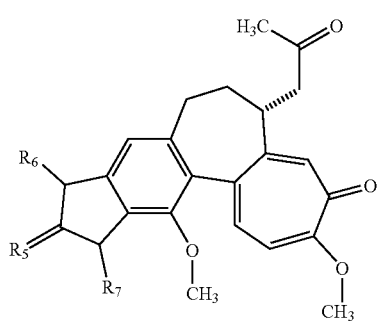

Formula 3 wherein $R_5$ represents a sulfur or an oxygen atom, wherein $R_6$ and $R_7$ individually represent a hydrogen or a substituent;

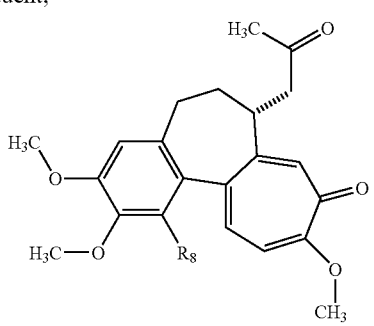

Formula 4 wherein $R_8$ represents a hydrogen or a substituent;

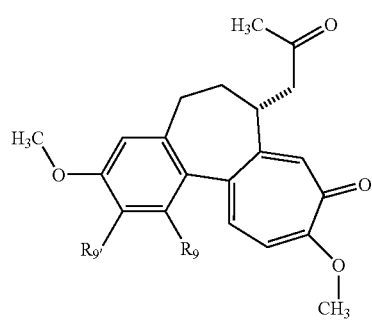

Formula 5 wherein $R_9$ and $R_{9'}$ individually represent a hydrogen or a substituent;

Formula 6 wherein $R_{10}$ represents sulfur or oxygen, wherein $R_{11}$, $R_{11}$ and $R_{11}$ individually represent a hydrogen or a substituent;

Formula 7 wherein $R_{14}$ represents a hydrogen or a substituent, and a pharmaceutically acceptable salt of a compound represented by Formulas 1 to 7.

BRIEF DESCRIPTION OF THE DRAWINGS

FIG. 1 shows certain amino acid sequences for beta tubulins that occur in both human beings and plasmodial protests.

DETAILED DESCRIPTION

Compounds useful for the treatment of malaria are provided which are derivatives of colchicine. The structure of colchicine is presented, e.g., at page 2438 of "The Merck Index," Tenth Edition (Merck & Co., inc., Rahway, N.J., 1983). As is disclosed in such publication, colchicine is N-(5,6,7,9-Tetrahydro-1,2,3,10-tetramethoxy-9-oxobenzo [a]hetalen-7-yl)acetamide; it has a molecular weight of 399.43 and an empirical formula of $C_{22}H_{25}NO_6$. The structural formula of colchicine is presented below; wherein the "numbering scheme" of atoms used in the following structural formula differs from the numbering scheme described in the Merck Index.

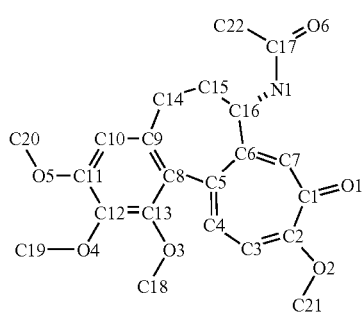

The following are exemplary embodiments of derivatives of colchicine.

Formula 1

In an exemplary embodiment, a colchicine derivative of the following Formula 1 is provided. Also provided is a pharmaceutically acceptable salt thereof. In Formula 1, the colchicine has been modified, for example, by the addition of a benzene ring.

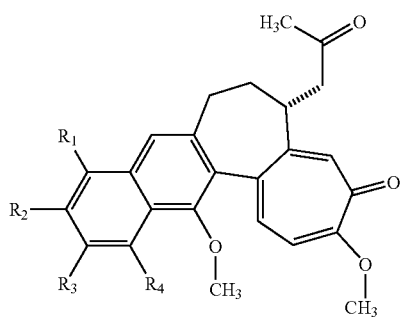

Formula I

In Formula 1, $R_1$ to $R_4$ represents hydrogen or a substituent. The substituent can include any suitable substituent such as one that is commonly present in substituted benzenes. Reference may be had to U.S. Pat. Nos. 3,876,632, 4,451,674 (substituted benzene derivatives); 4,467,126 (process for the preparation of a di-substituted benzene); 4,552,894 (2-fluoroethoxy-substituted benzene derivatives); 4,571,441 (process for separation of substituted benzene isomers); 4,962,252 (alkenyl-substituted benzene derivatives); 5,670,691 (method for making a substituted benzene compound); and 6,579,577 (substituted benzene derivative).

For example, the substituent can include a thiol group, a hydroxyl group, a lower alkyl group containing from 1 to 8 carbon atoms, a lower alkenyl group containing from 1 to 8 carbon atoms, a lower alkynyl group containing from 1 to 8 carbon atoms, —CN, —CF$_3$, NH$_2$, NO$_2$, hydroxyl, halogen, pentadiene, $C_1$-$C_{12}$ alkyl ester of an unsaturated carboxylic acid, methyl, ethyl, allyl, lower alkyl, lower alkyl interrupted by —O—, —S—, —SO— or —SO$_2$, N-methyl, N-ethyl, cycloalkyl, cycloalkyl-alkyl having up to 8 carbon atoms, benzyl, phenethyl, phenylpropyl mono- or di-substituted in the phenyl nucleus thereof by halogen, alkyl or alkoxy having 1 to 2 carbon atoms, amino, monomethylamino or dimethylamino, 2-furyl-methyl, 2-tetrahydrofuryl-methyl, pyridyl-methyl, trifluoromethyl, n-octyl-, n-dodecyl- or phenoxy group, $(CH_2CH_2CF_3)_n$ where n is at most 3, $C_1$-$C_6$, NH$_2$, C≡N—, oxygen, lower alkoxy group, a lower alkylthio group, a lower haloalkyl group, a lower haloalkylthio group, methylenedioxy group, alkenyl, and SO$_2$OR wherein R is alkyl, cycloalkyl, phenyl, $C_2$-$C_5$ alkyl, or isopropyl.

Formula 2

In another exemplary embodiment, a colchicine derivative of the following Formula 2 is provided. Also provided is a pharmaceutically acceptable salt thereof. Formula 2 differs from Formula 1 in that, instead of a benzene ring, it comprises a cycloalkane ring.

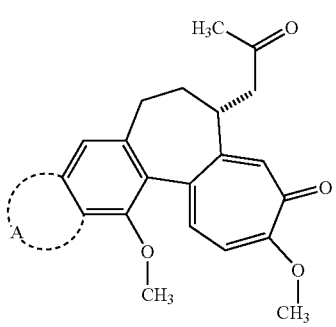

Formula 2 wherein A represents atoms for forming a cycloalkane ring, such as a cyclopropane ring, cyclobutane ring, cyclopentane ring, cyclohexane ring, cycloheptane ring, and cyclooctane ring, preferably a pentane ring, A can contain any number of substituents consistent with the number of carbon atoms present in A. A can be unsubstituted or substituted with at least one substituent. For example, the substituents can be selected from the list of substituents provided above in connection with $R_1$ to $R_4$.

Formula 3

In another exemplary embodiment, a colchicine derivative of the following Formula 3 is provided. Also provided is a pharmaceutically acceptable salt thereof.

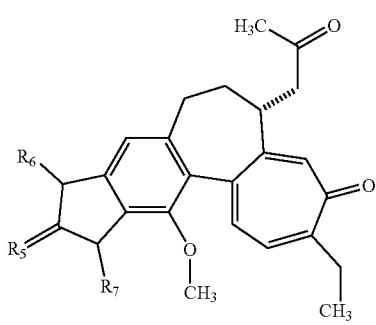

Formula 3

In formula 3, $R_5$ represents sulfur or oxygen, preferably oxygen. $R_6$ and $R_7$ individually represent hydrogen or a substituent. For example, $R_6$ and $R_7$ can be selected from the list of substituents provided above in connection with $R_1$ to $R_4$. In an alternative embodiment, $R_5$ can be switched in position in Formula 3 with $R_6$ or $R_7$.

Formula 4

In another exemplary embodiment, a colchicine derivative of the following Formula 4 is provided. Also provided is a pharmaceutically acceptable salt thereof. Formula 4 differs from colchicine in that the carbon atom 13 which normally carries an alkoxy group 20 is modified so that it can contain, for example, a thiol group (—SH).

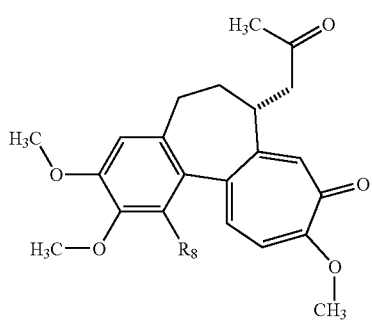

Formula 4

In Formula 4, $R_8$ represents a hydrogen, a thiol group, or any suitable substituent, preferably a thiol group. For example, $R_8$ can be selected from a hydroxyl group, a lower alkyl group containing from 1 to 8 carbon atoms, a lower alkenyl group containing from 1 to 8 carbon atoms, a lower alkynyl group containing from 1 to 8 carbon atoms, a —CN group, a halogen, alkoxy groups containing from about 2 to about 8 carbon atoms, methyl groups, and the substituents listed above in connection with $R_1$ to $R_4$.

Formula 5

In another exemplary embodiment, a colchicine derivative of the following Formula 5 is provided. Also provided is a pharmaceutically acceptable salt thereof. Formula 5 is, for example, an extension of Formula 3 wherein the alkane ring is opened.

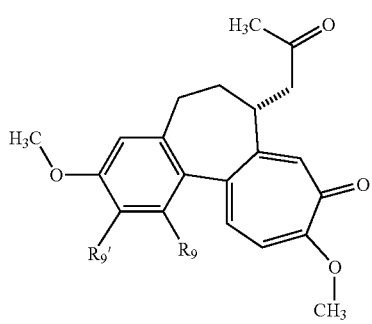

Formula 5

In Formula 5, $R_9$ and $R_{9'}$ each individually represents a hydrogen or a substituent. For example, $R_9$ and $R_{9'}$ can be selected from the list of substituents provided above in connection with $R_1$ to $R_4$.

Formula 6

In another exemplary embodiment, a colchicine derivative of the following Formula 6 is provided. Also provided is a pharmaceutically acceptable salt thereof. Formula 6 incorporates, for example, the features of Formulas 3 and 4 in combination, and may be optionally modified in any of the manners suggested above for Formulas 3 and 4.

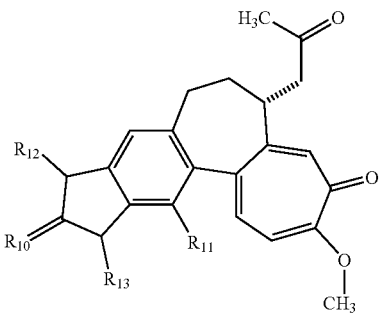

Formula 6

In Formula 6, $R_{10}$ represents a sulfur or oxygen. $R_{11}$, $R_{12}$ and $R_{13}$ each individually represents a hydrogen or a substituent. For example, the substituent can be selected from the list of substituents provided above in connection with $R_1$ to $R_4$.

Formula 7

In another exemplary embodiment, a colchicine derivative of the following Formula 7 is provided. Also provided is a pharmaceutically acceptable salt thereof. Formula 7 incorporates the features of Formula 5, for example, with an extended chain length.

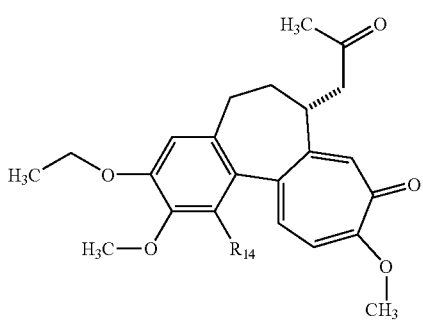

Formula 7

In Formula 7, $R_{14}$ represents a hydrogen or a substituent. For example, the substituent can be selected from the list of substituents provided above in connection with $R_1$ to $R_4$.

The colchicine derivative can be synthesized to have properties and characteristics to facilitate administration of such compound. The water solubility of the colchicine derivative can depend on the specific manner in which the colchicines derivative is employed. For example, the colchicine derivative compound can have a water solubility of at least 10 micrograms per milliliter, preferably at least 100 micrograms per milliliter, more preferably at least 500 micrograms per milliliter, more preferably at least 1,000 micrograms per milliliter, more preferably at least 2,500 micrograms per milliliter, more preferably at least 5,000 micrograms per milliliter, and more preferably at least 10,000 micrograms per milliliter. In an alternative embodiment, the colchicine derivative compound can have a water solubility of less than about 10 micrograms per milliliter, preferably less than about 1.0 micrograms per milliliter.

Solubility can be determined by any conventional means. For example, 0.5 milliliters of water can be mixed with the compound to be tested under ambient conditions and the mixture can be stirred for 18 hours under ambient conditions. The slurry thus produced can be filtered to remove the non-solubulized portion of the filtrand, and the amount of the filtrand that has been solubulized can be determined. From this, the number of micrograms that went into solution can be determined.

Without wishing to be bound to any particular theory, applicants believe that the presence of a hydrophilic group in the colchicine derivative compound of their invention can help render such compound water-soluble.

Formulations for administering colchicine derivatives may be prepared in accordance with conventional procedures, for example, the procedures described in U.S. Pat. No. 6,372,772. For example, known methods, materials and equipment for facilitating the administration of colchicine can be used in connection with the present colchicines derivatives.

In an exemplary embodiment, a method for administering a pharmacologically effective amount of a colchicine derivative to a mammalian host, preferably a human host, is provided. For example, an inhibitor of redox signaling (i.e., the NSC compounds described above) may be combined in vitro before administration or separately administered to the host with an anticancer agent, in either order, concurrently, or simultaneously, with administration generally taking place up to 24 hours after the administration of the other biological active agent(s). It should be noted that, in the composition of the instant application, in addition to a thioredoxin system inhibitor, or in place thereof, the inhibitor of redox activity can be employed.

The administration(s) can take place by any suitable technique including oral, subcutaneous and parenteral administration, preferably parenteral or oral, more preferably oral. For example, the colchicine derivative can be administered in the form of a pill or tablet. Examples of parenteral administration include intravenous, intraarterial, intramuscular and intraperitoneal, with intrapcritonal and intravenous being preferred. The dose and dosage regimen can depend on, for example, whether the inhibitors are being administered for therapeutic or prophylactic purposes, separately or as a mixture, the type of biological damage and host, the history of the host, and the type of inhibitors or biologically active agent. The amount is preferably effective to achieve an enhanced therapeutic index. For example, humans can be treated for relatively longer periods of time (in comparison with mice and rats) with a length depending on, for example, the length of the disease process and drug effectiveness.

The doses of the colchicine derivative can be single doses or multiple doses over a period of any number of days, and preferably in single doses. A protection level of at least 50% means that at least 50% of the treated hosts exhibited improvement against the disease or infection but not limited to improved survival rate, more rapid recovery, or improvement or elimination of symptoms. If multiple doses are employed, the frequency of administration can depend, for example, on the type of host, dosage amounts, etc. In some cases, daily administration can be effective, whereas in other cases, administration every other day or every third day can be more effective. The practitioner will be able to ascertain upon routine experimentation which route of administration and frequency of administration are most effective in any particular case. The dosage amounts for cancer which appear to be most effective herein are those that result in regression in size of the tumor or complete disappearance or non-reappearance of the tumor, and are not toxic or are acceptably toxic to the host patient. Generally, such conditions as fever, chills and general malaise can in some cases be considered acceptable. The optimum dose levels can also depend on sequence of administration, existing tumor burden, and the type of precursor.

An exemplary embodiment of the invention relates to the administration of a pharmaceutical composition (an inhibitor), in conjunction with a pharmaceutically acceptable carrier, for any of the therapeutic effects discussed above. Compounds and agents of the present invention, in connection with a pharmaceutically acceptable carrier, can be used for any of the therapeutic effects discussed above. Such compositions can be in the form of an agent in combination with at least one other agent, such as stabilizing compound which may be administered in any sterile, biocompatible pharmaceutical carrier, including, but not limited to, saline, buffered saline, dextrose, and water. The compositions may be administered to a patient alone or in combination with other agents, drugs or hormones.

In addition to the active ingredients, the pharmaceutical compositions can contain suitable pharmaceutically-acceptable carriers comprising, excipients and auxiliaries which facilitate processing of the active compounds into preparations which can be used pharmaceutically. Further details on techniques for formulation and administration may be found in the latest edition of *Remington's Pharmaceutical Sciences*, Maack Publishing Co., Easton, Pa.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by mammal or human.

Pharmaceutical preparations for oral use can be obtained through combination of active compounds with solid excipient, optionally grinding a resulting mixture and processing the mixture of granules, after adding suitable auxiliaries, if desired, to obtain tablets or dragee cores. Suitable excipients are carbohydrate or protein fillers, such as sugars, including lactose, sucrose, mannitol or sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins such as gelatin and collagen. If desired, disintegrating or solubilizing agents can be added, such as cross-linked polyvinyl pyrrolidone, agar, alginic acid, or a salt thereof such as sodium alginate.

Dragee cores can be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, for example, the dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starch, lubricant, such as talc or magnesium stearate, and optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension can also contain suitable stabilizers or agents which increase the solubility of the compounds to allow for the preparation of highly concentrated solutions.

For topical or nasal administration, penetrants appropriate to the particular barrier to be permeated can be used in the formulation. Penetrants which are known in the art can be employed in this regard.

The pharmaceutical compositions of the present invention can be manufactured by any suitable known means, for example, by means of conventional mixing, dissolving, granulating, dragee-making, levigating, emulsifying, encapsulating, entrapping, and/or lyophilizing processes.

The pharmaceutical composition may be provided as a salt and can be formed with many acids, including but not limited to hydrochloric, sulfuric, acetic, lactic, tartaric, malic, succinic, etc. Salts can tend to be more soluble in aqueous or other protonic solvents than the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, which can be combined with buffer prior to use.

After pharmaceutical compositions have been prepared, they can be placed in an appropriate container and labeled for treatment of an indicated condition, for administration Tr/Trx inhibitors, such labeling would include amount, frequency and method of administration.

Pharmaceutical compositions suitable for use in the invention include compositions wherein the active ingredients are contained in an effective amount to achieve the intended purpose. The determination of an effective dose can be within the capability of those skilled in the art.

For any compound the therapeutically effective dose can be estimated initially either in cell culture assays, for example, of neoplastic cells, or in animal models, usually mice, rabbits, dogs, or pigs. The animal model can also be used to determine the appropriate concentration range and route of administration. Such information can then be used to determine useful doses and routes for administration in humans.

The exact dosage can be determined by the practitioner, in light of factors related to the subject that requires treatment. Dosage and administration can be adjusted to provide sufficient levels of the active moiety or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks, depending on half-life and clearance rate of the particular formulation.

Normal dosage amounts can vary from 0.1 to 100,000 micrograms up to a total dose of about 1 gram, depending upon the route of administration. Techniques and methods for ascertaining particular dosages which are known to those skilled in the art can be employed in administering the compositions. The formulation processes and compositions described in U.S. Pat. No. 6,372,772 can also be used with regard to some, all, or none of the components of applicant's composition.

In an exemplary embodiment, the colchicine derivative compound can selectively and preferentially bind to a particular beta tubulin. The binding affinity of such colchicine derivative compound can be determined in accordance with the fluorescence binding assay that is described below.

The composition of this invention preferably is comprised of at least one anti-malarial drug that preferentially hinds to a beta-tubulin isotype.

One may obtain tubulin biological organisms and test the degree to which candidate drugs hind to the various tubulin isotypes by means well known to those skilled in the art. Reference is made to U.S. Pat. Nos. 5,661,032 (Tal alpha-tubulin promoter and expression vectors); 5,886,025 (anti-mitotic agents which inhibit tubulin polymerization); 6,000,772 (tubulin promoter regulates gene expression in neurons); 6,162,930 (anti-mitotic agents which inhibit tubulin polymerization); 6,258,841 (tubulin binding compounds [COBRA]); 6,306,615 (detection method for monitoring beta-tubulin isotype specific modification); 6,329,420 (tubulin binding compounds [COBRA]); 6,346,389 (method for selectively modulating the interactions between surviving and tubulin); 6,350,777 (description anti-mitotic agents which inhibit tubulin polymerization); 6,433,187 (certain polycyclic compounds useful as tubulin-binding agents); 6,586,188 (method for identification of compounds that bind to beta-tubulin and stimulate insulin secretion); 6,593,374 (tubulin binding ligands and corresponding prodrug constructs); 6,676,944 (vaccine containing a perioxiredoxin and/or a beta-tubulin); 6,694,436 (B-homoestra-1,3,5(10)-trienes as modulators of tubulin polymerization); and 6,750,330 (lypholized tubulins). The entire disclosure of each of the above U.S. patents is incorporated by reference herein.

In an exemplary embodiment, the activity of certain candidate drugs can be evaluated in the fluorescence binding assay as described in Israr A. Khan et al, *Differential Interaction of Tubulin Isotypes with the Antimitotic Compound IKP-104*, 39 Biochemistry at 9001-9009 (2000) (Khan et al). The experimental procedures described in Khan et al relate to an assay for assessing the binding if the anti-tumour drug IKP-104 to tubulin (pg 9002). These experimental procedures as discussed in Khan et al can readily be adapted to assess the binding of other anti-tubulin drugs.

As described in the "Materials" section of Khan et al, GTP purchased from Sigma Chemicals, located in St. Louis, Mo. (pg 9002), and IKP-104 synthesized at the K-I Research Institute (Shizuoka, Japan) are employed. The compound was dissolved in dimethyl sulfoxide immediately before use because repeated freezing and thawing led to a dramatic loss in its ability to bind tubulin and inhibit microtubule assembly. (Khan et al at 9002.)

In the section, "Purification of Tubulin Isotypes," Khan et al describes how microtubules were prepared from bovine cerebra by the method of Fellous et al and tubulin was purified therefrom by phosphocellulose chromatography. Phosphocellulose chromatography is a well known technique; reference may be had to U.S. Pat. Nos. 5,580,898 (method of stabilizing microtubules); 6,177,472 (regulation of alzheimer's disease proteins); 6,358,957 (phenylastin and the phenylastin analogs, a new class of anti-tumour compounds); 6,423,735 (compounds and methods for use thereof in the treatment of cancer); 6,423,736 (compounds and methods for use thereof in the treatment of cancer); 6,458,847 (method for screening for drugs useful in inhibition of polymerization of ab and tau peptides); 6,462,062 (compounds and methods for u. e thereof in the treatment of cancer); 6,482,043 (compounds and methods for use thereof in the treatment of cancer); 6,608,096(compounds and methods for use thereof in the treatment of cancer); 6,660,767 (coumarin compounds as microtubule agents and therapeutic uses thereof); 6,710,065; 6,713,480 (phenylastin and the phenylastin analogs, a new class of anti-tumour compounds); and 6,720,349(compounds and methods for use thereof in the treatment of cancer). The entire disclosures of the above U.S. patents are incorporated by reference herein.

Likewise, reference may be had to Khan et al which describes how microtubule-associated proteins were prepared from the microtubules and fractionated to purify tau by gel filtration as previously described. The isotypically purified abII, abIII, and abIV dimers were prepared by immunoaffinity chromatography as described previously. All isotypticallly purified tubulins were stored at −80° C. until they were ready for use. The immunoaffinity chromatography technique is described in U.S. Pat. Nos. 4,568,488 (reverse immunoaffinity chromatography); 5,316,932; 5,328,603; 5,362,857; and 5,614,500. The entire disclosures of the above U.S. patents are incorporated by reference herein.

In Khan et al, the relative amounts of alpha/beta III in each tubulin sample were measured by subjecting the tubulin to SDS-PAGE on 5.5% gels. The SDS-PAGE technique is referred to in U.S. Pat. Nos. 5,679,530 and 6,441,053, the disclosures of each of which are incorporated by reference herein.

In Khan et al, tubulin samples were reduced and carhoxymethylated prior to SDS-PAGE. Under these conditions, the beta III isotype has an electrophoretic mobility distinctly different from those of the beta II and beta IV isotypes, which comigrate. The immunoblotting of gels was carried out as previously described.

As discussed in Khan et al, the tubulin was thawed on ice-water and spun at 18000 g for 6 minutes at 4° C. to remove any insoluble tubulin aggregates from the sample. Tubulin present in the supernatant was quantitated by the method of described in O. H. Lowry et al., J. Biol. Chem. 193, 265-275 (1951), and mixed with IKP-104 and tau in MES buffer [0.1 M MES, 1 mM GTP, 0.5 mM MgCl2, 0.1 mM EDTA, 1 mM EGTA, and 1 mM b-mercaptoethanol (pH 6.4)] at 4° C. Unless otherwise mentioned, the final concentrations of tubulin and tau were 1.5 and 0.15 mg/mL, respectively. The temperature of the samples was raised from 4 to 37° C., and tubulin polymerization was followed by either sedimentation or turbidemetry as described previously.

In Khan et al the absorbance measurements were taken using a Beckman DU7400 spectrophotometer equipped with a Peliter temperature controller. The phenomenon of tubulin polymerization and means for effecting it or inhibiting it, are known to those skilled in the art. Reference may be had to U.S. Pat. Nos. 5,886,025 (anti-mitotic agents which inhibit tubulin polymerization); 6,162,930 (anti-mitotic agents which inhibit tubulin polymerization); 6,350,777 (description anti-mitotic agents which inhibit tubulin polymerization); and 6,964,436 (B-homoestra-1,3,5(110)-trienes as modulators of tubulin polymerization). The entire disclosures of each of the above U.S. patents are incorporated by reference herein.

The tubulin samples were then subjected to fluorescence analysis to determine the extent to which candidate drugs interacted with the tubulin. As disclosed in U.S. Pat. No. 6,660,767 (the entire disclosure of which is hereby incorporated by reference in to this specification), "the binding of dicoumarol was determined by taking advantage of the fluorescence properties of tubulin. Tubulin is a tryptophan containing protein. When excited, tubulin displays a typical tryptophan emission spectrum. An excitation wavelength was selected to specifically excite the tubulin tryptopanyl residues. Relative fluorescence intensities were measured and buffer blanks were subtracted from all measurements. By incubating tubulin with different concentrations of dicoumarol, whether there is concentration dependence between the binding of dicoumarol and the quenching of tubulin fluorescence was determined." See also Panda et al., 204 Eur. J. Biochem at 783-787 (1992); Panda et al., 94 PNAS USA at 10560-10564 (1997); and Panda et al, 272 J. Biol. Chem at 7681-7687 (1997), which are herein incorporated by reference. Reference may also be made to U.S. Pat. Nos. 5,851,789 and 6,472,541. The entire disclosures of each of the above U.S. patents are incorporated by reference herein.

As described in the section, "Electron Microscopy" of Khan et al, the mixtures of tubulin and tau were incubated for at least 20 minutes at 370° C. in the absence or presence of IKP-104 in MES buffer. The concentrations of tubulin and tau were 1.5 and 0.15 mg/mL, respectively. Aliquots (50 mL) were withdrawn and treated with 1% glutaraldehyde for 30 s, and then layered on 400-mesh copper grids coated with carbon over Formvar. After 1 minute, the grids were washed with 4 drops of water and stained with 1% uranyl acetate for 1 minute. Excess stain was removed, and after air-drying, grids were examined in a JEOL 100 CX electron microscope with an accelerating voltage of 60 kv.

In Khan et al, the IKP-104 Binding Assay was likewise described as follows. Tubulin (2 mM) and IPP-104 (0-25 mM) were mixed in 500 mL of 50 mM PIPES buffer (pH 7.0) containing 1 mM EGTA and 0.5 mM MgCl2. The mixture was incubated for 30 minutes at 30° C. and the fluorescence intensities of the samples were recorded in a Hitachi F-2000 spectrrofluorometer. The excitation and emission wavelengths were 273 and 330 nm, respectively. The absorbance of control samples containing 0-25 mM IKP-104 (was also measured at 273 and 330 nm to correct the absorbed fluorescence intensities at 330 nm for the inner filter effect. The corrected absorbed fluorescence data were analyzed by using different models and equations, wherein Kd1, Kd2, and Kd3 are the apparent dissociation constants for the high-, low-, and lowest affinity sites, respectively.

The fluorescence binding assay described in Khan et al is similar to an assay for assessing the binding of IKP-104 to tubulin reported in a 1998 paper by A. R. Chaudhuri et al. published in Biochemistry 37, 17157-17162. According to Khan et al, the Chaudhuri et al. assay "relies on the IKP-104-induced local conformational changes in tubulin and the increment of the fluorescence of IKP-104 fluorescence. However, the fidelity of this relationship appears to exist within a narrow range of IKP-104 concentrations (0-10 mM) because at higher concentrations (e.g., >10 mM IKP-104), instead of increasing, the IKP-104 fluorescence starts decreasing. In the method presented here, we have enhanced the reliability of the binding data by using a wider range of IKP-104 concentrations (0-25 mM) to obtain the near saturation of tubulin with the compound. Also, we have utilized the IKP-104-induced pertebrations in the intrinsic fluorescence of tubulin itself at 330 mm . . . as a probe for IKP-104 binding to the tubulin molecule."

In Khan et al, differential affinities of tubulin isotypes for IKP-104 were observed (page 9003). This observation was consistent with prior art discussed on page 9001 of the Khan et al where it was discussed that "both alpha and beta-subunits of tubulin differ as multiple isotypes. The differences among the beta-isotypes, which are found mostly within the C-terminal region, have been highly conserved throughout evolution. Tubulin dimers isotypically purified by their beta-subunits differ from each other in their assembly, dynamics, cellular distribution, post-translational modification, and conformation.

Disclosed on page 9001 of Khan et al, "some of the most interesting differences among the isotypes involve their interactions with ligands. The alpha/beta III dimer interacts much less strongly with colchicines, vinblastine, and paclitaxel than do the alpha/beta II and alpha/beta IV dimers."

In one preferred embodiment, an alpha/beta dimer selected from the group consisting of alpha/beta II, alpha/beta III, and alpha/beta V dimer is tested with candidate anti-tubulin agents at the "LC50" concentrations. As is known to those skilled in the art, the "LC50" is the concentration of the toxic compound that is lethal to 50% of the organism to be tested under the test conditions in a specified time. It is often also referred to as the "lethal concentration" or the "median lethal dose." Reference can be made to U.S. Pat. Nos. 5,470,822 (low-toxicity invert emulsion fluids); 5,549,840; 5,593,958; 5,599,785; 5,731,281; and 5,827,679. The entire disclosures of each of the above U.S. patents are incorporated by reference herein.

In an exemplary embodiment, the apparent dissociation constant for the high affinity site of the tubulin isotype in question can be determined. Without wishing to be bound to any particular theory, it is believed that the interaction of a drug with its receptors can be considered to follow what is termed "mass action kinetics." The interaction follows the Law of Mass Action, which requires the rates of chemical processes to relate systematically to the concentrations of the interacting compounds. Thus, if A+B interact to form AB, then the rate of the forward (f) reaction is dependant on a rate of constant, kf multiplied by the product of the concentrations A and B (Rate of forward reaction=kf [A][B]). By the same standard, the reverse (r) reaction is dependent on a rate constant, kr multiplied by the concentration of AB (Rate of reverse action=kr [AB]). At equilibrium, the rates of the forward and reverse reactions are equal. The ration kr divided by kf, is the equilibrium, or dissociation constant, commonly given the symbol Kd.

In the interaction of drugs with the protein tubulin, there are typically three binding sites, designated high affinity binding sites, low affinity binding sites, and very low affinity binding sites. The dissociation constants for interaction of drugs with these binding sites are given the symbols Kd1, Kd2, and Kd3 respectively. As is described in Khan et al, the rates of reaction, k and K values are studied and measured using fluorescence spectroscopy with excitation and emission wavelengths of 273 and 330 nm respectively, and mathematical analysis of the data generated.

Any particular drug can have a characteristic set of values for these three dissociation constants when interacting with a particular tubulin isotype. Thus a unique set of dissociation constant rations can be sought in the search for optimized interaction with certain tubulin isotypes.

Referring to page 9003 of Khan et al, it should be noted that, with regard to the alpha/beta III dimer, IKP-104, "the apparent dissociation constant for the high-affinity site (KdI) on alpha/beta IV was greater than those of unfractionated tubulin, alpha/beta II, or alpha/beta III. Both alpha/beta II and alpha/beta III had Kd1 values that were lower than that of unfractionated tubulin.

In one embodiment, the Kd1 value for a dimer selected from the group consisting of the abII dimer, the abIII dimer, and abV dimer is at least 1.1 times as great as the Kd1 value for unfractionated tubulin; in one embodiment, it is at least about 2.0 times as great as the Kd1 value for unfractionated tubulin.

The therapeutic indices of those candidate compositions that pass the binding affinity tests can be determined. For example, one can determine the therapeutic index by means well known to those skilled in the art. Reference can be made to U.S. Pat. Nos. 5,830,452 (method for enhancing the anti-tumor therapeutic index of interleukin-2); and 6,222,093 (methods for determining therapeutic index from gene expression profiles). The entire disclosures of each of the above U.S. patents are incorporated by reference herein.

The therapeutic index (TI) is described below with regard to cancer drugs, but it will be understood that such discussion can be equally applicable to anti-malarial drugs.

As is known to those skilled in the art, the therapeutic index (TI) assesses the margin of safety associated with the use of a drug. It can be measured in a variety of ways, in vitro and in vivo. For example, it can be expressed as: TI=IC50 in vitro killing non-cancer cells/IC50 in vitro killing cancer cells; and such index is preferably at least about 1.1 and more preferably at least about 2. In one embodiment, such index is at least about 5.0. In yet another embodiment, the therapeutic index is at least about 10.

The IC50 will be described, for purposes of illustration with regard to cancer drugs, but it will be understood that such discussion can be equally applicable to anti-malarial drugs.

As is known to those skilled in the art, the IC50 the concentration that inhibits growth of, or kills, 50% of the cells in a particular population in defined conditions (such as particular incubation medium, pH, temperature, etc.). Reference may be had to U.S. Pat. Nos. 5,466,620 (immunoassays for insulin sensitive enhancers); 6,025,331 (inhibitors of fibrin cross-linking and/or transglutaminases); 6,232,089 (CD23 processing enzyme preparation); 6,346,408 (method of allophycocyanin inhibition of enterovirus); 6,451,807 (methods of treating sexual dysfunction using a PDE5 inhibitor); 6,576,219 (method for enhancing outflow of aqueous humor in treatment of glaucoma); 6,620,818 (method for reducing the severity of side effects of chemotherapy); 6,630,492 (lymphocyte function antigen-1 antagonists); and 6,635,434 (immunoassay for pesticides and their degradation products). The entire disclosures of each of the above U.S. patents are incorporated by reference herein.

The IC50 derives from the sigmoid (S-shaped) graph of response (expressed as percent of cells inhibited) vs. log. concentration. The IC50 is the antilog. of the logarithm of the concentration of drug associated with a 50% response.

The therapeutic index can also be expressed as the ratio of any convenient measure of toxicity (or side effect) of a drug to any convenient measure of the desired effect of that drug in a laboratory animal such as the mouse. For example, the drug can have antimitotic activity at x mg/kg, but cause respiratory paralysis at y mg/kg. In this case: TI=y/x.

Similarly, the therapeutic index can be measured in humans. For example, the drug of the previous paragraph might cause a skin rash in humans at, say, 2y mg/kg, but need only 0.5x mg/kg to kill tumors, and not cause respiratory paralysis in humans. In this case: TI 2y/0.5x=4y/x. Thus the TI will be a different number depending on the circumstances of its measurement, in vitro, in animals or in humans. Generally speaking, a drug will need at least a ten-fold margin of safety (TI) in humans in vivo and while other measurements of TI may be important in the process of drug discovery only the human, in vivo, in patients, TI is of significant in therapeutics. In an exemplary embodiment, the goal is an infinitely high TI, and this can be attainable with highly selective tubulin inhibition.

One can evaluate candidate drugs to determine their suppressivity with various tubulin dimers comprised of an alpha isotype and a beta isotype. It is preferred that the alpha isotypes be selected from the group consisting of human alpha 1, human alpha 2, human alpha 3, human alpha 4, human alpha 6, human alpha 8, and the human equivalent of mouse alpha TT1. It is preferred that the beta isotype be selected from the group consisting of human class IA, human class Ib, human class 2, human class 3, human class 4a, human class 4b, human class 5, human class 6, and human class 7.

In the process of this invention, the effects of various colchicine derivatives upon the assembly and disassembly of microtubules can be determined. Assembly into microtubules is a first parameter that can be examined. This assembly will be described with reference to, e.g. cancer drugs, it being apparent that such discussion can be equally relevant to anti-malarial drugs.

In the presence of either tau or MAP2, alpha/betaII and alpha/betaIII assemble more rapidly and to a greater extent than does alpha/betaIV. See, e.g., the article by A. Banerjee et al., "Preparation of a monoclonal antibody specific for the class IV isotype of beta-tubulin. Purification and assembly of alpha/beta II, alpha/beta III, and alpha/beta IV tubulin dimers from bovine brain." (267 J. Biol. Chem. at 5625-5630).

In the absence of MAPs, but in the presence of 4 M glycerol, alpha/betaII and alpha/betaIV assemble rapidly with no lag time, while alpha/betaIII assembles only after a considerable lag time. See, e.g. an article by Q. Lu et al., "In vitro analysis of microtubule assembly of isotypically pure tubulin dimers. Intrinsic differences in the assembly process of alpha/betaII, alpha/betaIII, and alpha/betaIV tubulin dimers in the absence of microtubule-associated proteins." (269 J. Biol. Chem. at 2041-2047 (1994)). Microtubules formed from abIII are considerably more dynamic than those formed from either alpha/beta II or alpha/beta IV (see a 1994 article by D. Panda et al. "Microtubule dynamics in vitro are regulated by the tubulin isotype composition," Proc. Nat. Acad. Sci. USA 91, 1158-1362). Possibly consistent with these findings is that the intrinsic GTPase activity of tubulin is highest for alpha/beta III than for either alpha/beta II or alpha/beta IV (see a 1997 article by A. Banerjee, "Differential effects of colchicine and its B-ring modified analog MTPT on the assembly-independent GTPase activity of purified b-tubulin isoforms from bovine brain," Biochem. Biophys. Res. Commun. 231, 698-700). However, during microtubule assembly in the absence of MAPs, alpha/betaIII hydrolyzes GTP more slowly than do the other two dimers (see 1998 article by Q. Lu et al., "Structural and functional properties of tubulin isotypes," Adv. Struct. Biol. 5. 203-227).

It is preferred that the colchicine derivative of this invention have a binding affinity to the beta-tubulin isotypes that are preferentially present in *Plasmodium* species of at 3/1 and, more preferably, at least 5/1. In one embodiment, the relative Kd values are at least about 10/1. In another embodiment, the relative Kd values are at least about 50/1. In yet another embodiment, the relative Kd values are at least about 100/1.

It is also preferred that the colchicine derivative of this invention have a therapeutic index of at least 3/1 and more preferably at least 5/1. In one embodiment, the TI value is at least 10/1 and, more preferably at least about 50/1. In yet another embodiment, the TI value is at least about 100/1.

What is claimed is:

1. A colchicine derivative represented by one of the following Formulas 1 to 7:

Formula 1 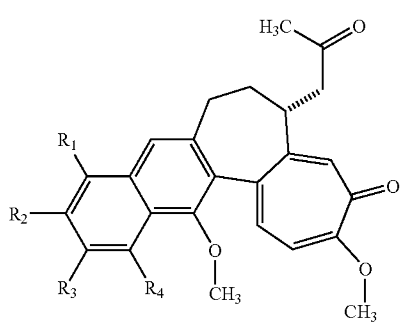 wherein $R_1$ to $R_4$ individually represent a hydrogen or a substituent;

Formula 2

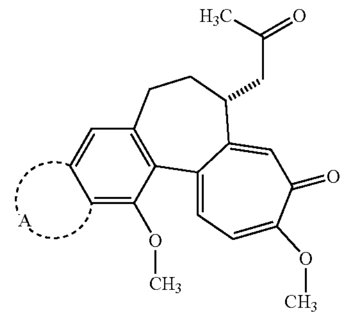

Formula 5 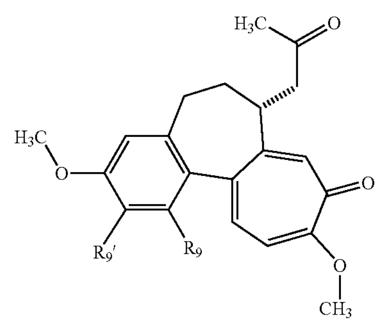 wherein $R_9$ and $R_{9'}$ individually represent a hydrogen or a substituent;

Formula 6 wherein $R_{10}$ represents sulfur or oxygen, wherein $R_{11}$, $R_{12}$ and $R_{13}$ individually represent a hydrogen or a substituent;

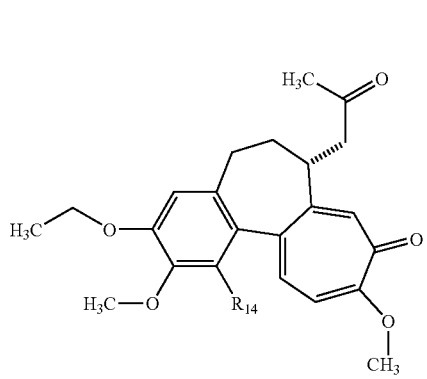

Formula 7 wherein R$_{14}$ represents a hydrogen or a substituent, and wherein A represents atoms for forming a cycloalkane ring, wherein A is substituted or unsubstituted;

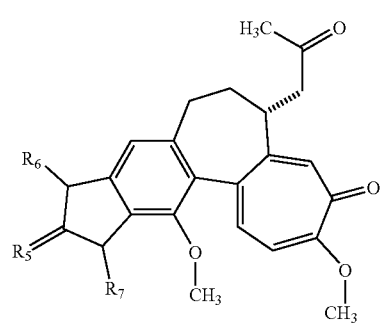

Formula 3 wherein R$_5$ represents a sulfur or an oxygen atom, wherein R$_6$ and R$_7$ individually represent a hydrogen or a substituent;

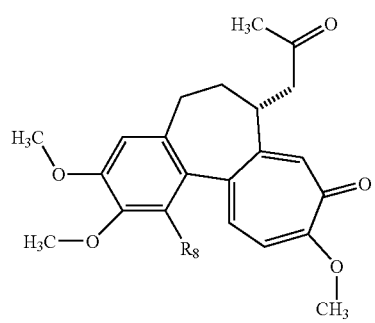

Formula 4 wherein R$_8$ represents a hydrogen or a substituent; a pharmaceutically acceptable salt of a compound represented by Formulas 1 to 7.

2. The colchicine derivative of claim 1, wherein the colchicine derivative is represented by Formula 2, and wherein A represents atoms for forming a cyclopropane ring, cyclobutane ring, cyclopentane ring, cyclohexane ring, cycloheptane ring or cyclooctane ring.

3. The colchicine derivative of claim 2, wherein A represents atoms for forming a cyclopentane ring.

4. The colchicine derivative of claim 1, wherein the colchicine derivative is represented by Formula 4, and wherein R$_8$ represents —SH.

5. The colchicine derivative of claim 1, wherein the colchicine derivative is represented by Formula 5, and wherein R$_9$ represents —SH.

6. The colchicine derivative of claim 1, wherein the colchicine derivative is represented by Formula 6, and wherein R$_{11}$ represents —SH.

7. The colchicine derivative of claim 1, wherein the colchicine derivative is represented by Formula 7, and wherein R$_{14}$ represents —O—CH$_3$.

8. A pharmaceutical composition comprising the colchicine derivative of claim 1, and a pharmaceutically acceptable carrier.

9. A method for treatment or prophylaxis of malaria in a mammal, comprising administering to the mammal a therapeutically effective amount of a composition comprising the colchicine derivative of claim 1.

10. The method of claim 9, wherein the mammal is a human.

11. The method of claim 9, wherein the therapeutically effective amount of the composition comprising the colchicine derivative is present in a tablet or a pill.

* * * * *